United States Patent [19]

Mukogawa et al.

[11] Patent Number: 4,786,473

[45] Date of Patent: Nov. 22, 1988

[54] APPARATUS FOR MEASURING IMPURITIES IN PURE WATER

[75] Inventors: Yasukazu Mukogawa; Katsuhikoa Tamura; Takaaki Fukumoto, all of Itami, Japan

[73] Assignee: Mitsubishi Denki Kabushiki Kaisha, Tokyo, Japan

[21] Appl. No.: 911,353

[22] Filed: Sep. 24, 1986

[30] Foreign Application Priority Data

Sep. 24, 1985 [JP] Japan .................. 60-211573

[51] Int. Cl.$^4$ ............................. G01N 33/18
[52] U.S. Cl. ......................... 422/68; 422/82; 436/53; 210/87; 73/61 R
[58] Field of Search ............. 422/68, 93, 82; 436/52, 436/53, 148; 210/340, 341, 87; 73/61 R, 53, 61.4, 28

[56] References Cited

U.S. PATENT DOCUMENTS

| | | |
|---|---|---|
| 3,200,700 | 8/1965 | Topol .................. 73/61 R |
| 3,236,095 | 2/1966 | Gelder . |
| 3,452,586 | 7/1969 | Childs et al. . |
| 3,499,315 | 3/1970 | Marino . |
| 3,605,485 | 9/1971 | Badzioch et al. .......... 55/270 |
| 3,872,710 | 3/1975 | Louvel ................ 73/61.4 |
| 3,997,297 | 12/1976 | Jenkins et al. ............ 422/93 |
| 4,117,715 | 10/1978 | Hoenig .................. 73/28 |
| 4,117,717 | 10/1978 | Isley . |
| 4,175,426 | 11/1979 | Rosenblum ............. 73/61.4 |
| 4,263,805 | 4/1981 | Isley et al. . |
| 4,361,028 | 11/1982 | Kamiya et al. ............. 73/28 |
| 4,446,726 | 5/1984 | Hockenberry ........... 73/61.4 |
| 4,521,864 | 6/1985 | Characklis . |
| 4,550,591 | 11/1985 | Cox et al. ................ 73/28 |
| 4,554,822 | 11/1985 | Eisenhauer et al. ........ 73/61 R |

FOREIGN PATENT DOCUMENTS

1598395 7/1970 Fed. Rep. of Germany .
2916036 11/1980 Fed. Rep. of Germany .

OTHER PUBLICATIONS

Japanese Abstract of Patent No. 76891-78; Jul. 1978.
German literature references to Vom Wasser (pp. 252-261) (1932); and to GWF-Glosser/Abwasser (pp. 220-222); (1976).
German references 1946505 and 1726563 as listed in German novelty search.
Literature ref. of Chem. Techn. (pp. 748-750); Dec. 1972.
"SDI Method", Handotai Process Zairyo Jitsumu Binran, p. 438, published by Science Forum Company, Apr. 25, 1983.

Primary Examiner—Michael S. Marcos
Assistant Examiner—Jill Johnston
Attorney, Agent, or Firm—Lowe, Price, LeBlanc, Becker & Shur

[57] ABSTRACT

An apparatus for measuring the concentration of solids in a flow of water is described. Water in a sampling pipe 2 is divided into two paths by a branch pipe. Water flowing through respective paths then passes through respective filters having different pore sizes. Then, the flow rates of the water passing through each of the filters 9a and 9b is measured by flow meters. An operation circuit successively calculates the relative ratio of the time dependent change of the output from each of the flow meters based on the outputs from each of the flow meters 10a and 10b. The successive ratios are indirectly related to the concentration of solids in the stream large enough to be captured by the smallest pore size filter.

6 Claims, 2 Drawing Sheets

APPARATUS FOR MEASURING IMPURITIES IN PURE WATER

BACKGROUND OF THE INVENTION

1. Field of the Invention

The present invention relates to an apparatus for measuring impurities in water, and more particularly to an apparatus for measuring solids content of water indirectly based on the time dependent change of the flow rate of water passing through a pair of filters having different pore sizes.

2. Description of the Prior Art

Conventionally, a direct microscopic method, FI (Fourier Index) value method (disclosed as SDI method in Handoutai Process Zairyo Jitsumu Binran p. 438 published by Science Forum Company, Apr. 25, 1983) and the like have been known as methods for evaluating the quality of pure water. According to the first mentioned method, pure water passes through a filter of 0.2 μm pore hole diameter and minute particles on the filter are examined with a microscope. According to the second mentioned method, a prescribed amount of pure water passes through a filter of 0.45 μm pore hole diameter under a constant pressure and the passing through time is measured.

It is known that among impurities in water there are materials having extremely small particle diameters such as colloidal materials. However, in the above described direct microscopic method, only particles larger than 0.2 μm can be captured, so that the aforementioned colloidal materials can not be measured. In addition, much labor and skill are required in the measurement. In the FI value method, only a filter having a pore diameter larger than 0.45 μm is used at present in consideration of the time required for filtering. Accordingly, in the FI value method, only minute particles larger than 0.45 μm can be captured, so that the aforementioned colloidal materials can not be measured. In addition, neither of the above described methods is capable of continuous monitoring in the field where the water is used so that neither can cope with a sudden change in the quality of water.

SUMMARY OF THE INVENTION

It is an object of the present invention to provide an apparatus for measuring the concentration of solid impurities in water in an extremely simple and continuous manner and which is also capable of measuring impurities of small particle diameter.

Briefly stated, according to the present invention, water from a sampling pipe is divided into two paths, water flowing through respective paths passes through respective filters and then the flow rates thereof downstream of the respective filters are measured. Then, the relative ratio of time dependent change in the flow rate of pure water passing through one filter to the time dependent change of flow rate of pure water passing through the other filter is successively calculated.

Namely, the present invention is adapted to measure the concentration of solid impurities in water indirectly by examining the time dependent change of the flow rate passing through one filter and the time dependent change of the flow rate of water passing through the other filter over a long period of time. In consideration of the fact that if there are such impurities in pure water, the filter will become clogged with the captured particles, the flow ratae of the water passing through the filter will decrease as time passes.

According to the present invention, the concentration of solid impurities in water can be measured without any skill in an extremely simple and continuous manner in the field where the water is used. Accordingly, a sudden change in the quality of pure water can be detected. In addition, even if the particle diameter of the impurity is small, the filter will become clogged gradually as the water passes through the filter over a long time, so that even in this case the measurement of impurity can be carried out. In addition, accurate measurement of the concentration levels of such impurities can be carried out continually even if the pressure or flow rate of the water fluctuates during measurement. The present invention provides two filters of different pore size and evaluates the relative ratios of time dependent changes in the flow rate of the water passing through respective filters.

These objects and other objects, features, aspects and advantages of the present invention will become more apparent from the following detailed description of the present invention when taken in conjunction with the accompanying drawings.

DESCRIPTION OF PREFERRED EMBODIMENTS

Figure 1:
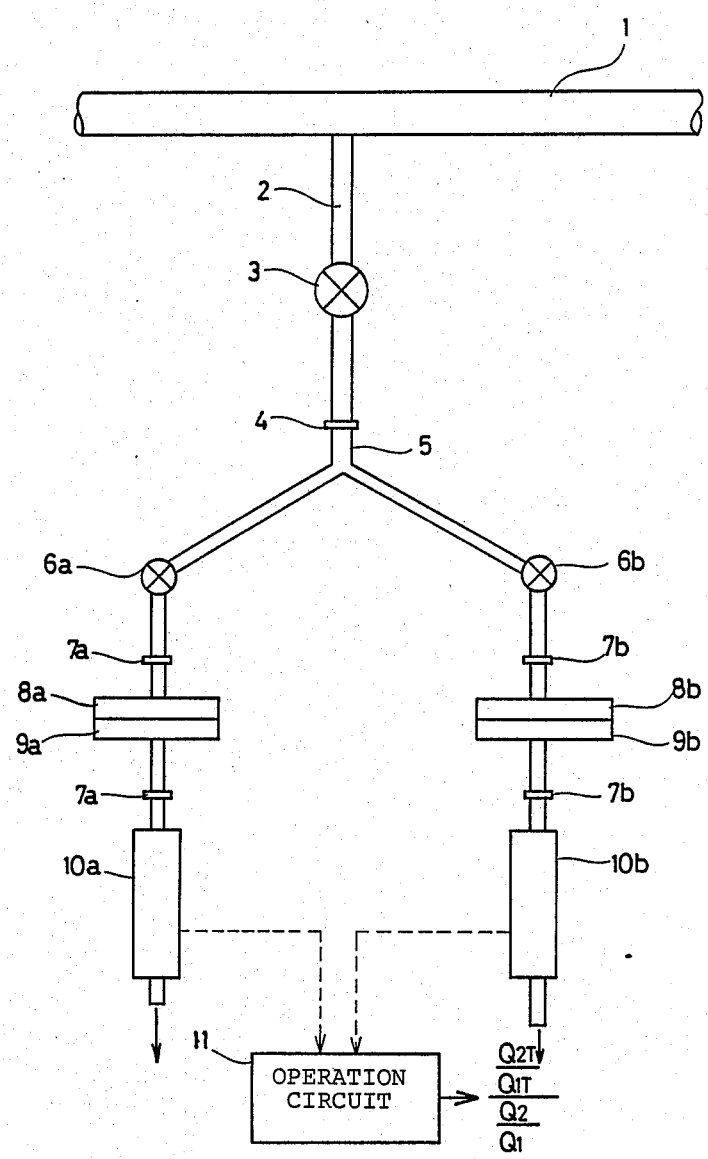
FIG. 1 is a schematic diagram showing the structure of one embodiment of the present invention.

FIG. 1 is a schematic diagram showing the structure of one embodiment of the present invention. In this figure, water which is actually used in the field passes through a conduit 1. A sampling pipe 2 is coupled to the water conduit 1. The sampling pipe 2 diverts water flowing through the conduit 1 to an impurity measuring apparatus. A manually operated valve 3 is provided in sampling pipe 2. A branch tube 5 is coupled to the sampling pipe 2 by means of joint 4. This branch pipe 5 divides the water flowing through the sampling pipe 2 into two paths. A valve 6a is provided in one path of the branch pipe 5 and a valve 6b is provided in the other path of the pipe 5. These valves 6a and 6b can be opened and closed manually. A first filter assembly is coupled to one path of the branch pipe 5 by a pair of joints 7a, and a second filter assembly is coupled to the other path by a pair of joints 7b. The first filter assembly comprises a filter holder 8a and a filter 9a. Filter holders 8a and 8b detachably hold the filters 9a and 9b, respectively. A membrane filter, for example, may be used for the filters 9a and 9b. Numerous minute pores are formed in respective filters 9a and 9b. The pore diameter of respective filters are selected to be different from each other. For example, the pore diameter of the filter 9a may be selected to be 0.1μ while the pore diameter of the filter 9b may be selected to be 1.0μ. Water which is filtered by the filter 9a is guided to a flow meter 10a and the flow rate thereof is measured. Water which is filtered by the filter 9b is guided to a flow meter 10b and the flow rate thereof is measured. The result of measurements of flow meters 10a and 10b are applied to an operation circuit 11. The operation circuit 11 calculates the relative ratio of the time dependent change in the flow rate measured by the flow meter 10a to the time dependent change in the flow rate measured by the flow meter 10b.

The operation and the method for use of the above described embodiment will be hereinafter described.

First, the filter 9a is attached to the filter holder 8a and the filter 9b is attached to the filter holder 8b. The first filter assembly is coupled to one path of the branch 5 by means of the joints 7a and the second filter assembly is coupled to the second path of the branch pipe 5 by means of the joints 7b. Then, manual valves 3, 6a and 6b are gradually opened to adjust the flow rate of water, which is flowing through the sampling pipe 2 and the branch pipe 5, at a predetermined rate.

Now let us assume that in the initial state, the flow rate of the water measured by the flow meter 10a and $Q_1$ and the flow rate of the water measured by the flow meter 10b is $Q_2$. Flow rates of water continuously measured by the flow meters 10a and 10b at each time are $Q_{1T}$ and $Q_{2T}$, respectively. These data are processed by the operation circuit 11 in the following manner. Namely, the operation circuit 11 calculates the value of $(Q_{2T}/Q_{1T})/(Q_2/Q_1)$ at prescribed time intervals. The evaluated value is the relative ratio of the time dependent change in the flow rate of the water passing through the filter 9a to the time dependent change of the flow rate of the water passing through the filter 9b. In the initial state, $Q_1=Q_{1T}$ and $Q_2=Q_{2T}$, so that the value calculated by the operation circuit 11 is 1. As more and more impurities in pure water are captured at the filters 9a and 9b, the flow rate of water passing through respective filters decreases, so that the evaluated value of the operation circuit 11 gradually becomes smaller than 1. Therefore, the change in the relative ratio evaluated by the operation circuit 11 indirectly indicates the concentration level of impurities in the water. Accordingly, evaluation of the level of impurities in the water can be carried out by examining the change of this relative ratio.

The output from the operation circuit 11 can be used in various ways. For example, it may be plotted on a chart by a XY plotter, etc. or it may be recorded on a recording medium such as a floppy disc or cassette tape for subsequent data analysis by a computer.

Figure 2:
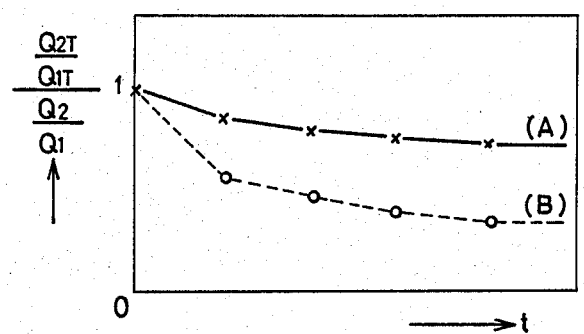
FIG. 2 is a graph showing a result of measurement of impurity levels of waters of different quality according to the embodiment of FIG. 1.

FIG. 2 is a graph showing one example of the output from the operation circuit plotted on the chart. As shown, the relative ratio evaluated by the operation circuit 11 is 1 in the initial state (t=0) and it becomes smaller as time passes. FIG. 2 shows the result of the measurement of two different waters (A) and (B). The value of the water (B) shown by the dotted line gradually becomes smaller than the value of the water (A) shown by the solid line as time passes, which means that the quality of the water (B) is inferior to the quality of the water (A).

The concentration level of impurities in water can be measured by examining the time dependent change in the flow rate of water passing through only one filter. However, according to such methods, if the pressure or flow rate of the water flowing through the sampling tube 2 happens to fluctuate for some reason, the measurement after fluctuation become meaningless. On the contrary, according to the above embodiment, accurate measurements can be carried out even if the pressure or flow rate of the water fluctuates during measurement since water flowing through the sampling pipe 2 divided into two paths and filters are provided in respective paths to evaluate the relative ratio of the time dependent change in the flow rate of water passing through respective filters. Namely, the fluctuation of the pressure or the flow rate of water appears both in the denominator and the numerator of the relative ratio, so that it does not influence the calculated ratio due to cancellation in the fraction. In an extreme case, even if the flow rate of water becomes 0, only one measurement at that time is lost and the measurement of the level of impurities can be continued when the water flows again.

In addition, according to the above embodiment, when the filters 9a and 9b are clogged, they can be replaced by new filters by detaching joints 7a and 7b. Therefore, the device can be used repeatedly, enabling continuous monitoring, and sudden change in the quality of water can be found.

By filtering water through respective filters 9a and 9b for a long period of time (for example one to several tens of days), the filters are gradually clogged even if the particle diameter of the impurity is small, so that the measurement of such impurities having small particle diameter can be carried out. If a filter having small pore diameter (for example less than 0.1 μm) is used as either of the filters 9a or 9b, it will be more effective.

Although in the above described embodiment, measurement of the level of impurities in pure water was described, the present invention can be applied to the measurement of the level of impurities in liquid chemicals provided that the filters 9a and 9b are chemically inert.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for measuring the concentration level of solid impurities in water of at least a predetermined minimum size, comprising
    a sampling pipe for guiding water whose concentration level of impurities is to be measured,
    branch means for dividing water flowing through said sampling pipe into first pipe means and second pipe means, said branch means being operatively connected to said sampling pipe and said first pipe means and said second pipe means,
    a first filter means of a predetermined pore size for filtering water flowing through said first pipe means and operatively connected thereto,
    first flow rate detecting means for detecting the flow rate of water filtered through said first filter means, said first detection means operatively connected to said first pipe means at a point near said first filter means,
    a second filter means for filtering water flowing through said second pipe means and operatively connected thereto, said second filter means having a smaller pore size than said first filter means;
    second flow rate detecting means for detecting the flow rate of water filtered through said second filter means, said second detecting means being operatively connected to said pipe means at a point near said second filter means; and
    operation means for successively calculating the relative ratio of the time dependent change in the flow rate of water detected by said first flow rate detecting means to the time dependent change in the flow rate of water detected by said second flow rate detecting means, whereby the concentration level of solid impurities which will not pass through said second filter means can be measured.

2. The apparatus of claim 1, wherein the pore size of said second filter is about 10 times smaller than the pore size of said first filter.

3. The apparatus of claim 1, wherein the pore size of said second filter is no larger than about 1 micron.

4. The apparatus of claim 3, wherein the pore size of said second filter is no larger than about 0.1 micron.

5. The apparatus of claim 1, wherein the pore size of said first filter is at least about 0.1 micron.

6. The apparatus of claim 5, wherein the pore size of said first filter is at least about 1 micron.

* * * * *

UNITED STATES PATENT AND TRADEMARK OFFICE
CERTIFICATE OF CORRECTION

PATENT NO. : 4,786,473

DATED : November 22, 1988

INVENTOR(S) : Yasukazu MUKOGAWA et al.

It is certified that error appears in the above-identified patent and that said Letters Patent is hereby corrected as shown below:

On the title page, please correct the spelling of the second named inventor to read as follows:

-- Katsuhiko Tamura --.

Signed and Sealed this

Fourth Day of July, 1989

*Attest:*

DONALD J. QUIGG

*Attesting Officer*  *Commissioner of Patents and Trademarks*